United States Patent [19]

Nishida et al.

[11] Patent Number: 5,576,431

[45] Date of Patent: Nov. 19, 1996

[54] METHOD FOR PRODUCTION OF PERFLUORO-CYCLIC IMINE

[75] Inventors: Masakazu Nishida, Nagoya; Takashi Abe, Kasugai; Haruhiko Fukaya, Oobu, all of Japan

[73] Assignee: Agency of Industrial Science & Technology, Ministry of International Trade & Industry, Tokyo, Japan

[21] Appl. No.: 568,509

[22] Filed: Dec. 7, 1995

[30] Foreign Application Priority Data

Dec. 13, 1994 [JP] Japan ..................... 6-332947

[51] Int. Cl.⁶ .................... C07D 265/30; C07D 211/72
[52] U.S. Cl. ...................... 544/98; 546/249; 548/565; 540/484
[58] Field of Search ................ 544/98; 546/249; 548/565

[56] References Cited

U.S. PATENT DOCUMENTS 3,235,561  2/1966  Haszeldine et al. .............. 546/249

OTHER PUBLICATIONS

Chemistry Letters, No. 5, pp. 905–908, 1989, Takashi Abe, et al., "An Alternative New Route to Perfluorovinylamines. Pyrolysis of an Alkali Metal Salt of Perfluoro(3–Dialkylamino–Propionic Acids)".

The Journal of Organic Chemistry, vol. 28, pp. 2811–2814, Sep.–Dec. 1963, John B. Hynes, et al., "The Indirect Fluorination of Some Halogenated Aliphatic Nitriles".

Journal of the Chemical Society, vol. 6, pp. 1098–1103, 1972, R. E. Banks, et al., "N–Fluoro–Compounds. Part IV. Photochemical and fluoride–Initiated Reactions Between Perfluoro–N–Fluoropiperidine and Perfluoropropene".

*Primary Examiner*—Robert W. Ramsuer
*Attorney, Agent, or Firm*—Oblon, Spivak, McClelland, Maier & Neustadt, P.C.

[57] ABSTRACT

A perfluoro-cyclic imine represented by the formula:

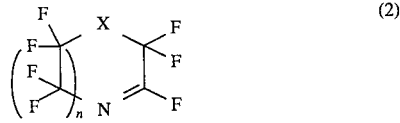

is produced by a method which comprises placing in a reaction vessel a perfluoro compound represented by the formula:

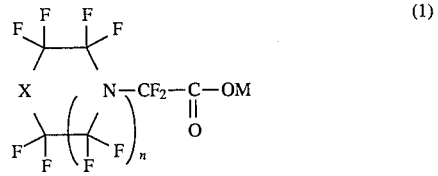

wherein X stands for one member selected from among $CF_2$, $CF(CF_3)$, and oxygen atom, M for one member selected from among monovalent alkali metal ions and alkaline earth metal ions, and n for 0, 1, or 2 and heating the perfluoro compound to a temperature in the approximate range of 100° C. to 500° C.

6 Claims, No Drawings

METHOD FOR PRODUCTION OF PERFLUORO-CYCLIC IMINE

BACKGROUND OF THE INVENTION

1. Field of the Invention

This invention relates to a novel method for the production of a perfluoro-cyclic imine. More particularly, this invention relates to a method for producing a perfluoro-cyclic imine useful as an intermediate for the synthesis of such fluorine-containing products as surfactants, agricultural pesticides, and medicines or a macromolecular monomer by the use of a readily available raw material, economically with a high yield.

2. Description of the Prior Art

In recent years, the fluorine-containing olefin compounds have been interested as intermediates or raw materials for the synthesis of various fluorine-containing products. They have been found extensive utility as intermediates for the synthesis of surfactants, agricultural pesticides, and medicines and as monomers for the production of fluorine-containing polymers.

Since perfluoro-cyclic imines, which are a type of such fluorine-containing olefin compounds, have a double bond between a carbon atom and a nitrogen atom in the cycle, they can easily react with a nucleophilic reagent. By using these compounds as intermediate raw materials, therefore, various compounds having a functional group linked to a nitrogen atom can be produced. Perfluoro-cyclic imine derivatives have been found useful for intermediates for surfactants, agricultural pesticides, and medicines.

Perfluoro-cyclic imines have already known in previous literatures and are produced by thermal decomposition of a corresponding secondary perfluoro-cyclic amine with/without a catalyst. Nonafluoro-2,3,4,5-tetrahydro-pyridine is produced from undecafluoropiperidine ["Journal of Organic Chemistry," p. 2811 (1963) and Journal of Chemical Society, Perkin I, p. 1098 (1972)], 2,2,3,3,5,6,6-heptafluoro-3,6-dihydro-2H-<1,4>oxazine from nonafluoromorpholine ["Journal of Chemical Society," p. 6077 (1965)], and heptafluoro-3,4-dihydro-2H-pyrrole from nonafluoropyrrolidine ["Journal of Organic Chemistry," p. 2811 (1963)]. The undecafluoropiperidine and the nonafluoromorpholine which are synthesized by the method of electrolytic fluorination from the corresponding cyclic amines only in low yields. The nonafluoropyrrolidine could not be synthesized by the method of electrolytic fluorination and is synthesized by the reaction of tetrafluorosuccinonitrile with silver (II) fluoride in low yield too.

It has been also known that nonafluoro-2,3,4,5-tetrahydro-pyridine and 2,2,3,3,5,6,6-heptafluoro-3,6-dihydro-2H-<1,4>-oxazine are synthesized in small amounts by the thermal decomposition from potassium perfluoropiperidinopropionate and potassium perfluoromorpholinopropionate, respectively ["Chemistry Letters," p.907 (1989)]. These reactions yield perfluoro(N-vinyl piperidine) and perfluoro(N-vinyl morpholine) as main products and the desired perfluoro-cyclic imines as by-products in such small amounts as 13 to 21%. Thermal decomposition of these propionate, therefore, does not prove a practical approach to the synthesis of perfluoro-cyclic imines.

A strong need is felt for the development of a method for producing a perfluoro-cyclic imine useful as an intermediate for synthesis and as a monomer for the production of fluorine-containing polymers from an easily procurable raw material, economically with a high yield.

It is, therefore, an object of this invention to provide a method for the production of a perfluoro-cyclic imine.

SUMMARY OF THE INVENTION

As a result of an extensive study, the present inventors learned that this object can be attained by using a trifluoroacetate having a cyclic perfluoroamino group as a raw material followed by this raw material to a heat treatment. This invention was accomplished as a result.

To be specific, this invention is directed to a method for the production of a perfluoro-cyclic imine represented by the formula:

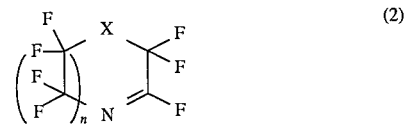
(2)

by placing in a reaction vessel a perfluoro compound represented by the formula:

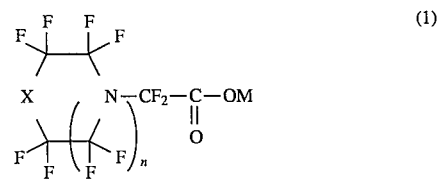
(1)

wherein X stands for one member selected from among $CF_2$, $CF(CF_3)$, and oxygen atom, M for one member selected from among monovalent alkali metal ions and alkaline earth metal ions, and n for 0, 1, or 2 and heating the perfluoro compound to a temperature in the approximate range of 100° C. to 500° C.

DESCRIPTION OF THE PREFERRED EMBODIMENTS

In the method of this invention, a trifluoroacetate having a cyclic perfluoroamino group represented by the formula (1) shown above is used as a raw material. The acetate mentioned above can be easily obtained by electrochemical fluorination of an acetic acid derivative represented by the formula:

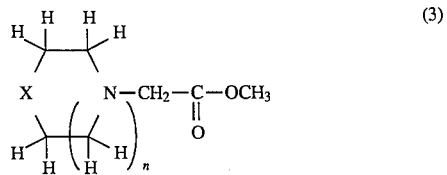
(3)

wherein X stands for one member selected from among $CF_2$, $CF(CF_3)$, and oxygen atom, and n for 0, 1, or 2, in hydrogen fluoride, hydrolyzation of the fluorination product, and reaction of hydroxides of an alkali metal or an alkaline earth metal with the hydrolyzate.

The compound represented by the formula (2) mentioned above can be easily obtained by thermal decomposition of a trifluoroacetate having a cyclic perfluoroamino group represented by the formula (1) mentioned above at a temperature in the range of 100° to 500° C. In this case, in order to proceed the thermal decomposition easily, a potassium salt is more favorable than other substituted trifluoroacetate salts.

The temperature of the thermal decomposition is properly selected in the range of 100° to 500° C., preferably 200° to 300° C. If the temperature is unduly high, the thermal decomposition tends to entail such side reactions as ring cleavage. If it is unduly low, the conversion is obtained at a low rate. The reaction time, though variable with the temperature of the treatment, generally falls in the range of from ten seconds to two hours. The reaction time decreases when the temperature of reaction is high. It is prolonged when the temperature of reaction is low.

The pressure of the reaction is not an important factor in the thermal decomposition reaction. This reaction can be carried out under a reduced pressure, under atmospheric pressure, or under an increased pressure, whichever best suits the occasion. The reaction is preferably performed under atmospheric pressure or under a reduced pressure in order to collect reaction product. The reaction of thermal decomposition is optionally carried out in the presence of a diluent, depending on the manner of conducting the reaction. Specific examples of the diluent usable herein include inert gases such as nitrogen, helium, argon, and carbon dioxide and nonprotonic liquid compounds such as polyethers, ethylene tetrachloride, and n-heptane. The ratio of dilution in this case is preferably not more than 100 times the original volume of the reaction mixture subjected to the dilution. For the sake of the thermal decomposition reaction, it is important that all the raw materials in use contain no water.

The method of this invention allows a perfluoro-cyclic imine to be obtained from a readily procurable raw material by a very simple process with a high yield. This method, therefore, is useful for commercial manufacture of a perfluoro-cyclic imine.

The perfluoro-cyclic imine thus obtained has a very high commercial value as an intermediate for the synthesis of such fluorine-containing products as surfactants, agricultural pesticides, and medicines and as a monomer for the production of fluorine-containing polymers.

This invention will now be described more specifically below with reference to working examples. It should be understood that this invention is not limited in any sense to or by these working examples.

EXAMPLE 1

Distilled water was placed in a three-neck flask equipped with a reflux condenser and a dropping funnel and a crude product of the electrolytic fluorination of methyl piperidinoacetate was added through the dropping funnel while the three-neck flask was kept cooled. The resultant hydrolyzate was extracted with ether from the reaction mixture, dried with anhydrous sodium sulfate, and then distilled under a vacuum in the presence of a small amount of concentrated sulfuric acid to obtain perfluoropiperidinoacetic acid (bp: 120° C./121 mmHg). This perfluoropiperidinoacetic acid was suspended in distilled water. The suspension was kept agitated by the use of a magnetic stirrer and an aqueous potassium hydroxide solution was added to the agitated suspension until pH 10. The resultant reaction mixture was deprived of water and low-boiling fractions by the use of an evaporator and then dried for one day with a vacuum pump to obtain white solid potassium perfluoropiperidino-acetate.

The 2.64 g (7.26 m.mols) of potassium perfluoro-piperidinoacetate thus obtained was placed in a round-bottomed flask having an inner volume of 50 ml. The top of the flask was connected through a collection trap to a vacuum pump. The flask, with the interior thereof vacuumized to 50 mmHg, was heated with a mantle heater to 280° C. over a period of 8 minutes. The flask was further kept at this temperature for 30 minutes to effect thermal decomposition of the potassium acetate. The product was collected as condensed with the trap, which was kept cooled with liquid nitrogen. This product was passed severally through traps cooled to −78° C., −110° C., and −173° C. and then separated as condensed under a vacuum of 1 mmHg. The desired nonafluoro−2,3,4,5-tetrahydro-pyridine was obtained at a yield of 81% in the traps cooled to −110° C. and −78° C. When the compound thus obtained was analyzed by gas chromatography (liquid phase: 1,6-bis(1,1,1,2-trihydroperfluorododecyloxy)hexane, carrier: 60 to 80 mesh Sucromosorb PAW, and carrier gas: helium), IR, $^{19}$F NMR, and Mass, the results were found to coincide with the spectroscopic data of the known nonafluoro-2,3,4,5-tetrahydro-pyridine [("Journal of Organic Chemistry," p.2811 (1963)].

EEXAMPLE 2

From a crude product of the electrochemical fluorination of ethyl morpholinoacetate, potassium perfluoromorpholinoacetate was obtained by following the procedure of Example 1.

The 2.64 g (7.26 m.mols) of potassium perfluoro-morpholinoacetate thus obtained was placed in a round-bottomed flask having an inner volume of 50 ml. The top of the flask was connected through a collection trap to a vacuum pump. The flask, with the interior thereof vacuumized to 50 mmHg, was heated with a mantle heater to 280° C. over a period of 10 minutes. The flask was further kept at this temperature for 30 minutes to effect thermal decomposition of the potassium acetate. The product was collected as condensed with the trap, which was kept cooled with liquid nitrogen. This product was passed severally through traps cooled to −78° C., −110° C., and −173° C. and then separated as condensed under a vacuum of 1 mmHg. The desired 2,2,3,3,5,6,6-heptafluoro-3,6-dihydro-2H-<1,4>oxazine was obtained at a yield of 71% in the trap cooled to −110° C. When the compound thus obtained was analyzed by gas chromatog-raphy (liquid phase: 1,6-bis(1,1,1,2-trihydroperfluorododecyloxy)hexane, carrier: 60 to 80 mesh Sucromosorb PAW, and carrier gas: helium), IR, $^{19}$F NMR, and Mass, the results were found to coincide with the spectroscopic data of the known 2,2,3,4,5,6-heptafluoro-3,6-dihydro-2H-<1,4>oxazine ("Journal of Chemical Society," p. 6077 [(1965)].

EXAMPLE 3

From a crude product of the electrochemical fluorination of ethyl pyrrolidinoacetate, potassium perfluoropyrrolidinoacetate was obtained by following the procedure of Example 1.

The 2.48 g (7.44 m.mols) of potassium perfluoro-pyrrolidinoacetate thus obtained was placed in a round-bottomed flask having an inner volume of 50 ml. The top of the flask was connected through a collection trap to a vacuum pump. The flask, with the interior thereof vacuumized to 50 mmHg, was heated with a mantle heater to 270° C. over a period of 25 minutes. The flask was further kept at this temperature for 30 minutes to effect thermal decomposition of the potassium acetate. The product was collected as condensed with the trap, which was kept cooled with liquid nitrogen. This product was passed severally through traps cooled to −78° C., −110° C., and −173° C. and then separated as condensed under a vacuum of 1 mmHg. The desired heptafluoro-3,4-dihydro-2H-pyrrole was obtained at a yield of 60% in the trap cooled to −110° C. When the compound thus obtained was analyzed by gas chromatography (liquid phase: 1,6-bis(1,1,1,2-trihydroperfluorododecyloxy)hexane, carrier: 60 to 80 mesh Sucromosorb PAW, and carrier gas: helium), IR, $^{19}$F NMR, and Mass, the results were found to coincide with the spectroscopic data of the known heptafluoro-3,4-dihydro-2H-pyrrole [("Journal of Organic Chemistry," p. 2811 (1963)].

We claim:

1. A method for the production of a perfluoro-cyclic imine represented by the formula:

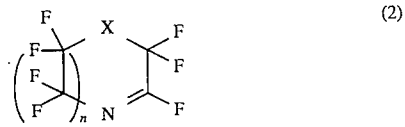

(2)

by placing in a reaction vessel a perfluoro compound represented by the formula:

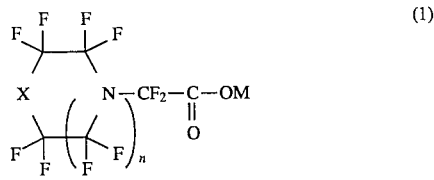

(1)

wherein X stands for one member selected from among $CF_2$, $CF(CF_3)$, and oxygen atom, M for one member selected from among monovalent alkali metal ions and alkaline earth metal ions, and n for 0, 1, or 2 and heating the perfluoro compound to a temperature in the approximate range of 100° C. to 500° C.

2. The method according to claim 1, wherein the temperature of said heating is in the range of from 200° C. to 300° C.

3. The method according to claim 1, wherein M stands for a potassium ion.

4. The method according to claim 1, wherein said perfluoro compound is potassium perfluoropiperidinoacetate and said perfluoro-cyclic imine is nonafluoro-2,3,4,5-tetrahydro-pyridine.

5. The method according to claim 1, wherein said perfluoro compound is potassium perfluoromorpholinoacetate and said perfluoro-cyclic imine is 2,2,3,3,5,6,6-heptafluoro-3,6-dihyro-2H-<1,4>oxazine.

6. The method according to claim 1, wherein said perfluoro compound is potassium perfluoropyrrolidinoacetate and said perfluoro-cyclic imine is heptafluoro-3,4-dihydro-2H-pyrrole.

* * * * *